(12) United States Patent
O'Brien

(10) Patent No.: US 10,632,250 B2
(45) Date of Patent: Apr. 28, 2020

(54) FLUID DISPENSING DEVICE

(71) Applicant: KEYMED (MEDICAL & INDUSTRIAL EQUIPMENT) LTD., Essex (GB)

(72) Inventor: Colin O'Brien, Essex (GB)

(73) Assignee: KEYMED (MEDICAL & INDUSTRIAL EQUIPMENT) LTD. (GB)

( * ) Notice: Subject to any disclaimer, the term of this patent is extended or adjusted under 35 U.S.C. 154(b) by 127 days.

(21) Appl. No.: 15/520,482

(22) PCT Filed: Oct. 22, 2015

(86) PCT No.: PCT/GB2015/053165
§ 371 (c)(1),
(2) Date: Apr. 20, 2017

(87) PCT Pub. No.: WO2016/063066
PCT Pub. Date: Apr. 28, 2016

(65) Prior Publication Data
US 2017/0311781 A1    Nov. 2, 2017

(30) Foreign Application Priority Data

Oct. 22, 2014 (GB) .................................. 1418765.2

(51) Int. Cl.
*A61M 5/152* (2006.01)
*A61M 5/14* (2006.01)
(Continued)

(52) U.S. Cl.
CPC .............. *A61M 5/152* (2013.01); *A61M 5/14* (2013.01); *A61M 5/148* (2013.01); *A61M 5/1452* (2013.01); *A61M 2005/14506* (2013.01)

(58) Field of Classification Search
CPC ...... A61M 5/14; A61M 5/142; A61M 5/1452; A61M 5/148; A61M 5/152; A61M 2005/14533; A61M 2205/12; A61M 5/145; A61M 2005/14506; A61M 2205/0216; B65D 83/0005; B65D 83/0055; B65D 83/0061; B65D 83/0072; B67D 1/0001;
(Continued)

(56) References Cited

U.S. PATENT DOCUMENTS 3,625,401 A    12/1971 Terry
4,157,771 A *  6/1979 Smith ................... A61M 5/148
                                                  100/265

(Continued)

FOREIGN PATENT DOCUMENTS

BE        1017668 A3    3/2009

OTHER PUBLICATIONS

Inellectual Property Office< Application No. GB1418765.2, Patents Act 1977: Search Report under Section 17, dated Mar. 24, 2015.

*Primary Examiner* — Shefali D Patel
(74) *Attorney, Agent, or Firm* — Luedeka Neely Group, PC

(57) ABSTRACT

A device for dispensing a fluid from a flexible bag includes a casing containing a tray for receiving the flexible bag and a pressure applicator movable by an actuator. Movement of the actuator pushes the pressure applicator against the tray by translation or by rotation to compress the bag between the tray and the casing.

7 Claims, 3 Drawing Sheets

(51) Int. Cl.
*A61M 5/145* (2006.01)
*A61M 5/148* (2006.01)

(58) Field of Classification Search
CPC ... B67D 1/0462; B67D 7/0216; B67D 7/0255
See application file for complete search history.

(56) References Cited

U.S. PATENT DOCUMENTS

| | | | |
|---|---|---|---|
| 4,613,327 A | | 9/1986 | Tegrarian et al. |
| 4,645,094 A | * | 2/1987 | Acklin ................ A47K 5/1217 |
| | | | 222/103 |
| 4,899,911 A | * | 2/1990 | Rohde ................ B67D 1/0001 |
| | | | 222/103 |
| 5,135,646 A | | 8/1992 | Tanokura et al. |
| 5,281,202 A | | 1/1994 | Weber et al. |
| 5,472,420 A | | 12/1995 | Campbell |
| 6,948,636 B1 | * | 9/2005 | Fischer ................ A61M 5/148 |
| | | | 222/103 |
| 2004/0026448 A1 | * | 2/2004 | Pichotte ................ A61M 5/148 |
| | | | 222/95 |

* cited by examiner

FLUID DISPENSING DEVICE

CROSS-REFERENCE TO RELATED APPLICATION

This application claims priority under all applicable statutes, and is a U.S. National phase (37 U.S.C. Section 371) of International Application PCT/GB2015/053165, filed Oct. 22, 2015, and entitled FLUID DISPENSING DEVICE, which claims priority to GB 1418765.2, filed Oct. 22, 2014, incorporated herein by reference in their entireties.

The present invention relates to a device for dispensing fluid from a flexible bladder, preferably at substantially constant pressure.

Various medical procedures, for example those carried out with endoscopes, require a flow of fluid to the medical instrument, which may be used to irrigate and clean a site in a patient's body. Pumps, such as peristaltic pumps, may be used in order to draw fluid from a reservoir and supply it to the medical instrument. However, such pumps tend to cause pulsing of the fluid flow, creating vibrations in the medical instrument.

The present invention provides a fluid dispensing device for dispensing fluid from a flexible bladder, comprising first and second compression surfaces configured to receive a flexible fluid-filled bladder between them, and an actuator operable to move at least one compression surface towards the other compression surface, thereby to compress the bladder in use and to dispense fluid from it, wherein the actuator is configured to act on first and second opposed ends of the or each compression surface either simultaneously or independently, whereby the compression surface is selectively movable by translation or by rotation relative to the other compression surface.

The invention provides a simple device for evenly compressing a fluid-filled bladder in order to dispense fluid at substantially constant pressure.

Preferably, the or each movable compression surface comprises a body movably connected to the actuator by a linkage. The linkage may comprise at least two arms pivotally connected between the actuator and the body. The actuator may be axially extendible and upon extension, causes the arms of the linkage to move the body towards the other compression surface.

Alternatively, the actuator may comprise a rotatable shaft and an eccentric cam mounted thereon.

In a preferred embodiment, the device further comprises a casing for receiving the flexible bladder, wherein a first wall of the casing forms one compression surface. In this case, the actuator may be secured to a second wall of the casing and the second compression surface is movable by the actuator relative to the casing.

Preferably, the device also comprises at least one protective member locatable between the or each compression surface and the flexible bladder in use. This serves to protect the bladder from rupture and spreads the pressure evenly across its surface.

Preferably, the device also comprises sensing means operable to detect when the bladder is empty or close to empty.

The invention will now be described in detail, by way of example only, with reference to the accompanying drawings, in which.

Figure 5:
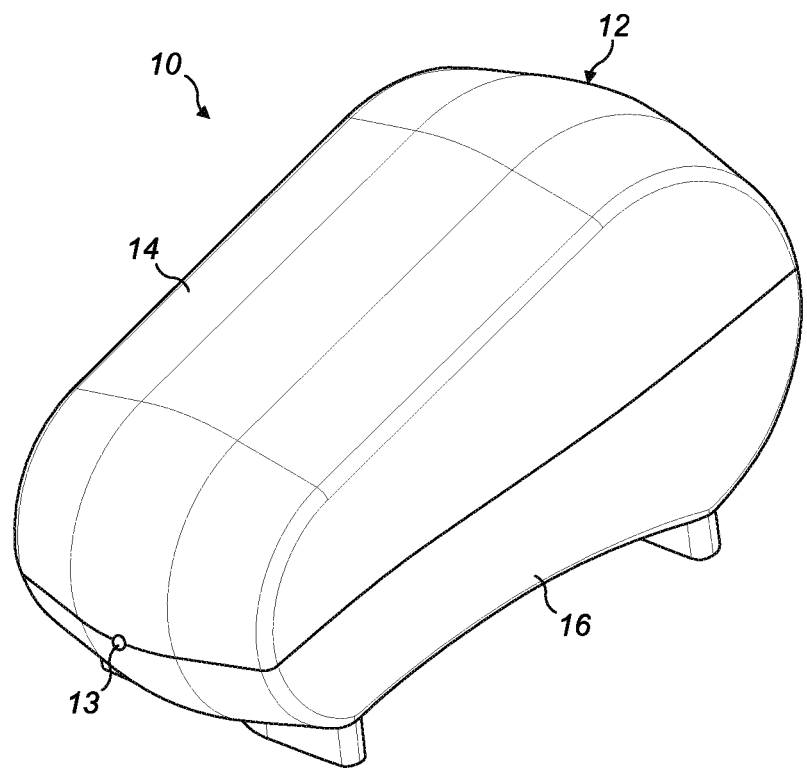
FIG. 5 is a perspective view of the casing in the closed position.

One embodiment of a fluid dispensing device 10 in accordance with the present invention comprises an openable casing 12. This may of clamshell type design with a base 14 and a lid 16 which are hinged together on one edge for movement between a closed and an open position. Some form of catch or lock (not shown) is provided to retain the base 14 and lid 16 in the closed position when desired. Even in the closed position an opening 13 is provided in the casing 12 for tubing for fluid being dispensed. For clarity this is only shown in FIG. 5.

A pressure applicator 18 is movably located in the base 14. A tray or receiving member 20 is provided within the casing 12. This may be loose or have some means to clip it into place adjacent the pressure applicator 18. A flexible bladder or bag 22 containing fluid, for example a plastic bag of saline with an outlet 24 for connection to tubing, can be received within the casing 12 between the tray 20 and part of the casing 12, in this example the interior surface of the lid 16.

The tray 20 is preferably a thin, flexible member, for example of plastic, which is shaped to conform with the shape of the flexible bag 22 when full, so that in use a full bag 22 will sit snugly within the tray 20. Thus, in this example, the tray 20 is substantially oval with a raised lip 21 around the edge. The surface receiving the bag 22 is generally concave, but may have a central, raised or convex part 23.

The pressure applicator 18 is an elongate body with a top surface 26 which contacts one side of the tray 20 in use. The pressure applicator 18 is connected via a linkage 28 to an actuator 30, which is secured within the base 14 of the casing 12. The linkage 28 in this example comprises two arms 32, 34 which are pivotally connected to opposite ends of the pressure applicator 18. The arms 32, 34 are also pivotally connected to opposite ends of the electrical actuator 30.

Figure 1:
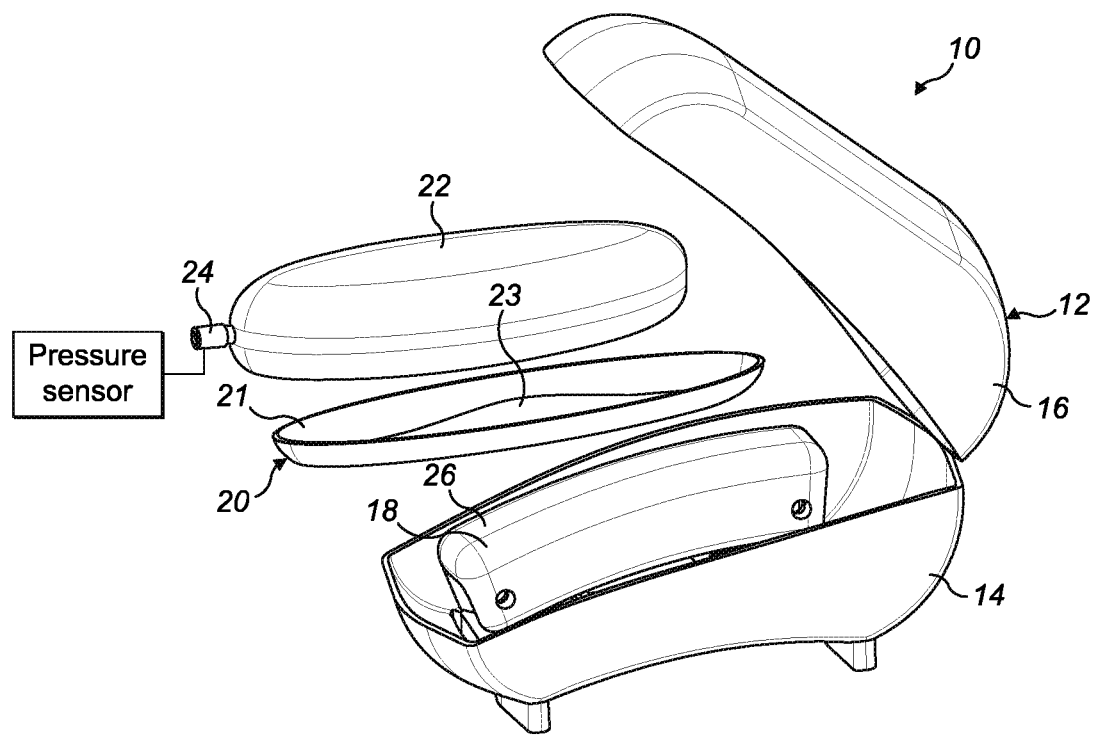
FIG. 1 is a perspective view of a fluid dispensing device in accordance with the present invention, in the open position and with some parts shown exploded for clarity.
Figure 2:
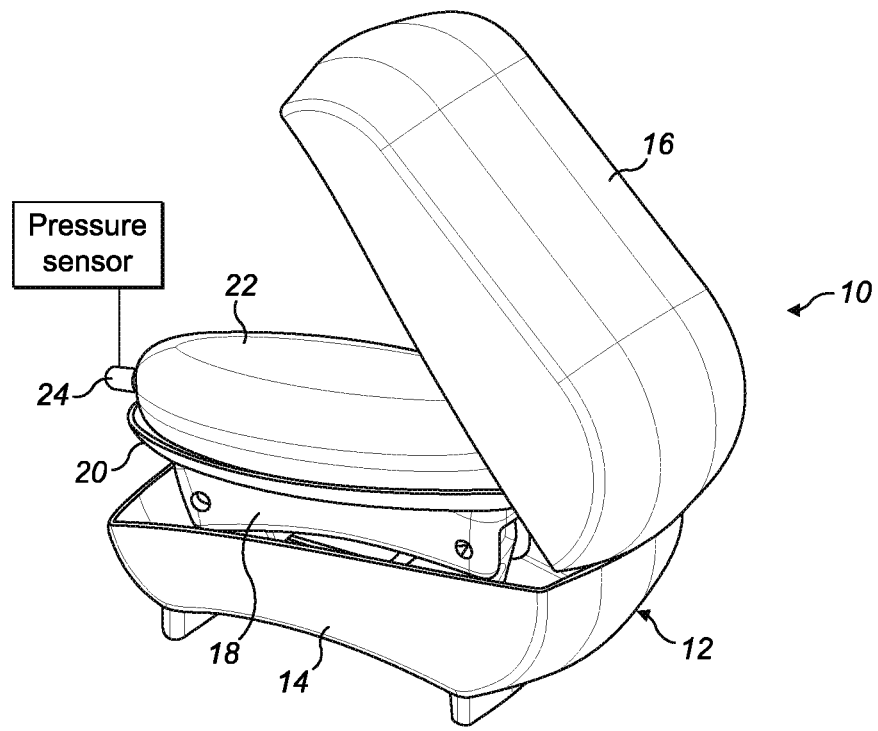
FIG. 2 is an alternative perspective view of the device, open and with the components in the starting position.
Figure 3:
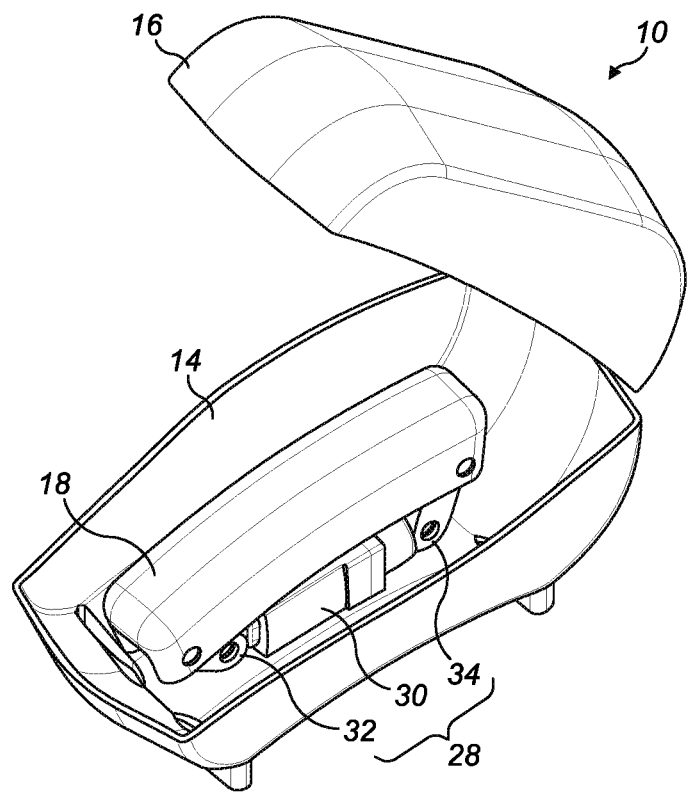
FIG. 3 is an alternative perspective view of the open casing and showing the pressure applicator.
Figure 4:
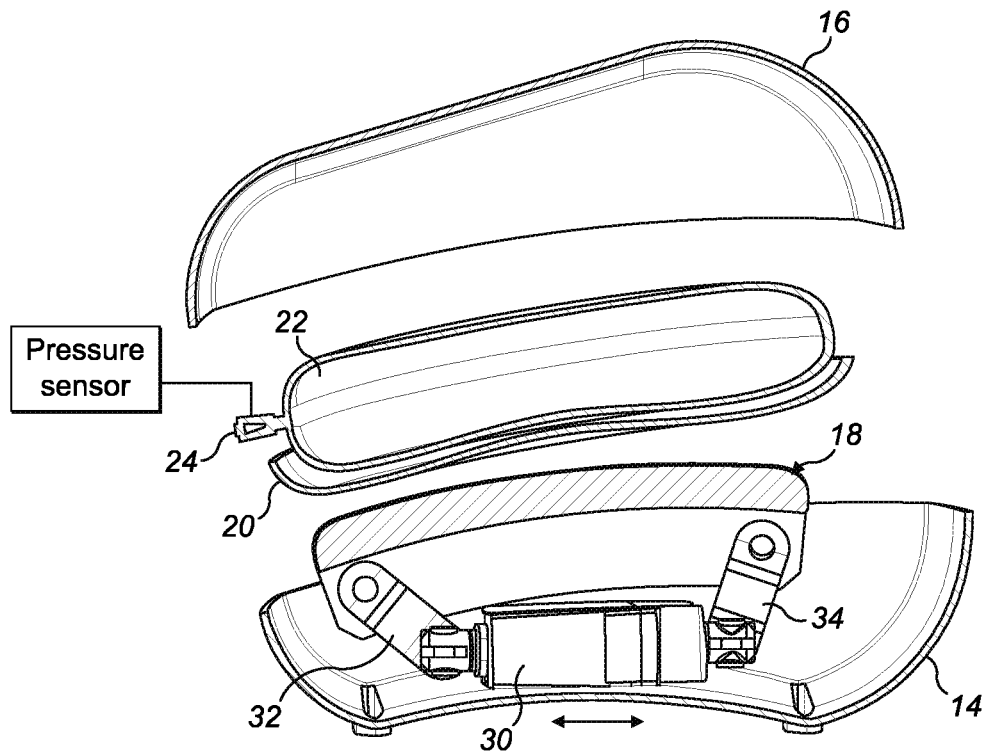
FIG. 4 is a side exploded view, with the casing shown in cross-section, to show further features of the pressure applicator.

The actuator 30 is axially extendible in the direction of the double-headed arrow in FIG. 4. As the actuator 30 extends, it pushes the arms 32, 34 away from each other. Since the arms 32, 34 are also connected to the pressure applicator 18, the arms rotate and cause the pressure applicator 18 to move upwardly (as seen in FIG. 4) away from the actuator 30 and the base 14 and towards the lid 16.

The actuator 30 is preferably electrical and may be battery or mains powered. The extendible ends of the actuator 30 may operate simultaneously or independently, so as the move the arms 32, 34 either simultaneously or independently of each other.

Thus, if both ends of the actuator 30 are extended together, the pressure applicator 18 is moved upwards evenly and it remains substantially parallel to the other compression surface, i.e. in this case, the interior of the lid 16, as it translates towards it.

Alternatively, one end of the actuator 30 can be extended before the other. For example, the right-hand end of the actuator 30 (as seen in FIG. 4) may be extended first causing the arm 34 to move upwardly, rotating the right-hand end of the pressure applicator 18 upwardly, compressing the end of the bag 22 which is furthest from the outlet 24. The pressure applicator 18 is then at an angle and no longer parallel to the lid 16. As the bag 22 becomes emptier, the left-hand of the actuator 30 may be extended, causing the arm 32 to move the left-hand end of the pressure applicator 18 upwardly as well. Thus, the pressure applicator 18 rotates back into a position in which it is substantially parallel to the lid 16. These movements of the pressure applicator 18 by translation and rotation help to empty the bag 22 fully and at substantially constant pressure.

The extension of the actuator 30 and thus movement of the linkage arms 32, 34 may be varied as desired. For example, if the bag 22 contains two or more substances, the ends could be compressed and released alternately to ensure mixing of the substances before they are dispensed.

In use, the casing 12 is opened and a bag 22 placed in position on the tray 20, which itself rests on the pressure applicator 18. The lid 16 is closed and secured to the base 14. The actuator 30 is operated so that the arms 32, 34 force the pressure applicator 18 towards the tray 20 and the bag 22, starting to compress the bag 22 between the tray 20 and the lid 16 and taking up any slack in the bag 22 ensuring that fluid within it is slightly pressurised. The tray 20 protects the bag 22 against rupture by spreading the pressure applied from the pressure applicator 18 across substantially the whole of one face of the bag 22. As the arms 32, 34 are movable independently as mentioned above, the arm 34 may be operated first, moving one end of the pressure applicator 18 to compress the end of the bag 22 which is furthest from the outlet 24.

The device 10 is then ready for use in a medical procedure. Increased extension of the actuator 30 forces the pressure applicator 18 further towards the lid 16. This continues to compress the bag 22 and thus dispenses fluid from it through the outlet 24. The actuator 30 continues to drive the pressure applicator 18 towards the lid 16 as the bag 22 empties and reduces in volume.

Preferably, means is provided to detect when the bag 22 is close to or completely empty. For example, this may be a pressure sensor on the outlet to detect the pressure of fluid being dispensed. It may be a pressure sensor within the tray 20 or pressure applicator 18 or a sensor measuring extension of the linkage 28 or proximity of the pressure applicator 18 to the lid 16. Any suitable form of sensing means is possible.

Once the bag 22 is empty or close to empty, the actuator 30 is retracted, returning the pressure applicator 18 to its starting position. The casing 12 is opened and the empty bag 22 removed and replaced with a full one.

The casing 12 may be configured so that it can be suspended in use so that gravity assists the flow of fluid from the outlet 24.

Figure 6A:
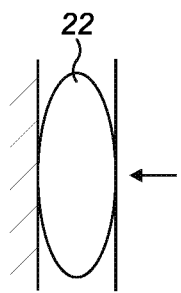
FIGS. 6a, 6b & 6c illustrate schematically various alternative mechanisms for operating the fluid dispensing device.
Figure 6B:
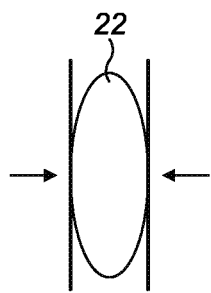

It will be appreciated that numerous alternatives are possible for the compression mechanism. In the example above, the bag 22 is compressed by between one fixed surface and one movable surface, as illustrated schematically in FIG. 6a. However, it is also possible to configure the device such that surfaces on both sides of the flexible bag can be moved towards each other, as illustrated schematically in FIG. 6b. The two movable surfaces may be operated by a common actuator so that they are moved together, or by independent actuators so that one surface can be moved at a time.

Figure 6C:
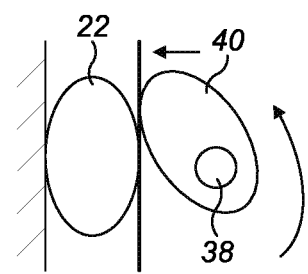

The form of the actuator 30 and the linkage 28 may be varied as desired. In place of an extendible actuator and pivoting arms, a rotating actuator 38 with an eccentric cam 40 mounted thereon could be used as illustrated schematically in FIG. 6c. Rotation of the actuator shaft 38 would rotate the cam 40, which would in turn force the pressure applicator 18 to move against the bag 22. The shaft 38 and eccentric cam 40 may be configured to apply pressure first towards one end of the pressure applicator 18, causing it to rotate, and subsequently to apply pressure in a central portion of the pressure applicator to cause translation. Two shafts 38 and cams 40 could also be used, one for each end of the pressure applicator 18, operable simultaneously or independently. This arrangement will provide for movement of the pressure applicator 18 either translating substantially parallel to the opposing compression surface, or moving one end before the other to provide rotational movement of the pressure applicator 18 relative to the other compression surface. These variations are of course not exhaustive and further possibilities will be apparent to the skilled person.

The invention claimed is:

1. A fluid dispensing device for dispensing a fluid from a flexible bladder, the fluid dispensing device comprising first and second compression surfaces configured to receive the flexible bladder between them, and an actuator operable to move the first compression surface towards the second compression surface, thereby to compress the flexible bladder in use and to dispense the fluid from the flexible bladder, wherein the first compression surface comprises first and second opposed ends and the actuator is connected to the first and second opposed ends, and the actuator is configured to act in two alternative modes of operation, wherein in a first mode of operation of the two alternative modes of operation the actuator acts simultaneously on the first and second opposed ends of the first compression surface in order to move the first compression surface by translation relative to the second compression surface; and in a second mode of operation of the two alternative modes of operation the actuator acts on only one of the first and second opposed ends of the first compression surface in order to move the first compression surface by rotation relative to the second compression surface.

2. The fluid dispensing device as claimed in claim 1, wherein a first arm is pivotally connected between the actuator and the first end of the first compression surface and a second arm is pivotally connected between the actuator and the second end of the first compression surface.

3. The fluid dispensing device as claimed in claim 2, wherein the actuator is axially extendible and upon extension causes the first and second arms to move the first compression surface towards the second compression surface.

4. The fluid dispensing device as claimed in claim 1, further comprising a casing for receiving the flexible bladder, wherein a first wall of the casing forms the second compression surface.

5. The fluid dispensing device as claimed in claim 4, wherein the actuator is secured to a second wall of the casing and the first compression surface is movable by the actuator relative to the casing.

6. The fluid dispensing device as claimed in claim 1, further comprising at least one protective member locatable between one or both of the first and second compression surfaces and the flexible bladder during use of the fluid dispensing device to dispense the fluid.

7. The fluid dispensing device as claimed in claim 1, further comprising sensing means operable to detect when the flexible bladder is empty of the fluid or close to empty of the fluid.

* * * * *